United States Patent [19]
Lai

[11] Patent Number: 5,869,348
[45] Date of Patent: Feb. 9, 1999

[54] METHODS FOR THE PREPARATION OF ANTIBODIES DIRECTED AGAINST DITHIOCARBAMATES AND THE USE THEREOF FOR DETECTION OF NITRIC OXIDE IN BODY FLUIDS

[75] Inventor: Ching-San Lai, Encinitas, Calif.

[73] Assignee: Medinox, Inc., San Diego, Calif.

[21] Appl. No.: 644,961

[22] Filed: May 15, 1996

[51] Int. Cl.[6] .................................................. G01N 33/558
[52] U.S. Cl. ................... 436/543; 424/178.1; 424/179.1; 424/181.1; 424/193.1; 424/600; 514/548; 436/547; 436/822
[58] Field of Search ................................ 514/548, 2, 22, 514/885; 424/178.1, 179.1, 181.1, 193.1, 194.1, 600; 436/547

[56] References Cited

U.S. PATENT DOCUMENTS

| | | |
|---|---|---|
| 4,472,301 | 9/1984 | Buckler et al. . |
| 4,493,795 | 1/1985 | Nestor, Jr. et al. . |
| 5,358,703 | 10/1994 | Lai . |
| 5,412,083 | 5/1995 | Giese et al. . |

OTHER PUBLICATIONS

Mashiba et al "Immunotargeting Approach Utilizing Production of Oxygen Free Radicals" *Cancer Letters* 55(3) 1990 pp. 183–188. Abstract.

Harlowe & Lane "Antibodies, A Laboratory Manual" Cold Spring Harbor Laboratory, USA. pp. 129–131, 1988.

Lesourd et al, Int J Immunopharmacology 10(2) 1988 pp. 135–144 Abstract only.

Bahouth et al., "Immunological approaches for probing receptor structure and function" *Trends Pharmacol. Sci.*, 12:338 (1991).

Benoit et al., "Presence of somatostatin–28–(1–12) in hypothalamus and pancreas" *Proc. Natl. Acad. Sci. USA*, 79:917–921 (1982).

Bredt and Snyder, "Nitric Oxide: A Physiologic Messenger Molecule" *Ann. Rev. Biochem.*, 63:175–95 (1994).

Downes et al., "Determination of a Non–volatile Nitrosamine by Using Denitrosation and a Chemiluminescence Analyser" *Analyst*, 101:742–748 (1976).

Galfre and Milstein, "Preparation of Monoclonal Antibodies: Strategies and Procedures" *Meth. Enzymol.*, 73:3–46 (1981).

Gretch et al., "The Use of Biotinylated Monoclonal Antibodies and Streptavidin Affinity Chromatography to Isolate Herpesvirus Hydrophobic Proteins or Glycoproteins" *Anal. Biochem.*, 163:270–277 (1987).

Hibbs, Jr. et al., "Evidence for Cytokine–inducible Nitric Oxide Synthesis from L–Arginine in Patients Receiving Interleukin–2–Theraphy" *J. Clin. Invest.*, 89:867–877 (1992).

Ignarro, L.J., "Biosynthesis and Metabolism of Endothelium–Derived Nitric Oxide" *Ann. Rev. Pharmacol. Toxicol.*, 30:535–560 (1990).

Ignarro et al., "Endothelium–derived relaxing factor produced and released from artery and vein is nitric oxide" *Proc. Natl. Acad. Sci., USA*, 84:9265–9269 (1987).

Kelm and Schrader, "Control of Coronary Vascular Tone by Nitric Oxide" *Cir. Res.*, 66(6):1561–1575 (1990).

Lai and Komarov, "Spin trapping of nitric oxide produced in vivo in septic–shock mice" *FEBS. Lett.*, 345:120–124 (1994).

Lancaster and Hibbs, "EPR demonstration of iron–nitrosyl complex formation by cytotoxic activated macrophages" *Proc. Natl. Acad. Sci. USA*, 87:1223:1227 (1990).

Lowenstein and Snyder, "Nitric Oxide, A Novel Biologic Messenger" *Cell*, 70:705–707 (1992).

Miles et al., "Association betweem biosynthesis of nitric oxide and changes in immunological and vascular parameters in patients treated with interleukin–2" *Eur. J. Clin. Invest.*, 24:287–290 (1994).

Moncada, S., "The 1991 Ulf von Euler Lecture: The L–arginine:nitric oxide pathway" *Acta Physiol. Scand.*, 145:201–227 (1992).

O'Shannessy et al., "A Novel Procedure for Labeling Immunoglobulins by Conjugation to Oligosaccharide Moieties" *Immunol. Lett.*, 8:273–277 (1984).

Palmer, R.., "The Discovery of Nitric Oxide in the Vessel Wall" *Arch. Surg.*, 128:396–401 (1993).

Palmer et al., "Nitric oxide release accounts for the biological activity of endothelium–derived relaxing factor" *Nature*, 327:524–26 (1987).

Radomski and Moncada, "Regulation of Vascular Homeostasis by Nitric Oxide" *Thromb. Haemos.*, 70(1):36–41 (1993).

Rodeberg et al., "Nitric Oxide: An Overview" *Am. J. Surg.*, 170:292–303 (1995).

Rodwell and McKearn, "Linker Technology: Antibody–Mediated Delivery Systems" *Biotech.*, 3:889–894 (1984).

(List continued on next page.)

*Primary Examiner*—Patricia Duffy
*Assistant Examiner*—Heather A. Bakalyar
*Attorney, Agent, or Firm*—Gray, Cary, Ware & Freidenrich; Stephen E. Reiter

[57] ABSTRACT

In accordance with the present invention, ELISA methods for the measurement of NO levels in mammalian body fluids utilizing monoclonal antibodies directed against dithiocarbamates and related iron complexes are described. It has been found that conjugation of dithiocarbamates to a macromolecule produces immunogenic dithiocarbamate-macromolecule derivatives. Such derivatives can be used for the production (e.g., in rodents) of monoclonal antibodies directed against different forms of dithiocarbamates (e.g., free dithiocarbamates, as well as complexes thereof with iron and, optionally, nitric oxide). In contrast, non-derivatized dithiocarbamates alone are not immunogenic. The simple, easy and non-invasive ELISA methods for measurement of NO levels in body fluids will find a variety of uses, e.g., for diagnosis and monitoring of NO overproduction that has been associated with many inflammatory and infectious diseases.

18 Claims, No Drawings

OTHER PUBLICATIONS

Shinobu et al., "Sodium N–Methyl–D–glucamine Dithiocarbamate and Cadmium Intoxication" *Acta Pharmacol et Toxicol.*, 54:189–194 (1984).

Vallance et al., "Direct measurement of nitric oxide in human beings" *Lancet*, 346:153–154 (1995).

Warnke and Levy, "Detection of T and B Cell Antigens with Hybridoma Monoclonal Antibodies: A Biotin–Avidin–Horseradish Peroxidase Method" *J. Histochem. and Cytochem.*, 28(8):771–776 (1980).

METHODS FOR THE PREPARATION OF ANTIBODIES DIRECTED AGAINST DITHIOCARBAMATES AND THE USE THEREOF FOR DETECTION OF NITRIC OXIDE IN BODY FLUIDS

FIELD OF THE INVENTION

The present invention relates to methods for the detection of nitric oxide in mammalian body fluids and reagents useful therefor. In one aspect, the present invention relates to methods for rendering non-immunogenic dithiocarbamates immunogenic. In another aspect, the present invention relates to methods for generating antibodies to dithiocarbamates, as well as the resulting antibodies. In yet another aspect, the present invention relates to methods for determining the tissue distribution of dithiocarbamates in a mammalian subject to which such compounds have been administered.

BACKGROUND OF THE INVENTION

Nitric oxide (NO), a gaseous free radical, was once considered mainly as an environmental pollutant from car exhausts and in city smog and cigarette smoke. This view toward nitric oxide was changed in 1987, the year in which NO was discovered to be produced in humans (see, for example, Ignarro et al., in Proc. Natl. Acad. Sci., USA, 84:9265–69 (1987) and Palmer et al., in Nature, 327:524–26 (1987)). First identified as an endothelium-derived relaxation factor, NO is now recognized as a new kind of cell signaling molecule that regulates the functions of many mammalian cells and tissues.

NO is generated by the enzymatic cleavage of L-arginine, catalyzed by the nitric oxide synthase enzyme (NOS; see, for example, Rodeberg et al., in Am. J. Surg., 170:292–303 (1995), and Bredt and Snyder in Ann. Rev. Biochem., 63:175–95 (1994)). Two major forms of NOS, constitutive and inducible enzymes, have been identified. Under physiological conditions, a low output of NO is produced by the constitutive, calcium-dependent NOS isoform (cNOS), which is present in numerous cells, including endothelium and neurons. This low level of nitric oxide is involved in a variety of regulatory processes, e.g., blood vessel homeostasis, neuronal communication and immune system functions. On the other hand, under pathophysiological conditions, a high output of NO is produced by the inducible, calcium-independent NOS isoform (iNOS), which is expressed in numerous cell types, including endothelial cells, smooth muscle cells and macrophages. These high levels of nitric oxide have been shown to be associated with many inflammatory and infectious diseases and conditions, such as septic shock, over expression of cytokines, diabetes, allograft rejection, inflammatory bowel disease, etc.

Nitric oxide is a potent vasodilator (see, for example, Palmer in Arch. Surg., 128:396–401 (1993) and Radomski & Moncada in Thromb. Haemos., 70:36–41 (1993)). For example, in blood, NO produced by the endothelium diffuses isotropically in all directions into adjacent tissues. As NO diffuses into the vascular smooth muscle, it binds to guanylate cyclase enzyme, which catalyzes the production of cGMP, inducing vasodilation (see, for example, Ignarro, L. J., Ann. Rev. Toxicol. 30:535–560 (1990); Moncada, S., Acta Physiol. Scand., 145:201–227 (1992); and Lowenstein and Snyder, Cell, 70:705–707 (1992)).

The overproduction of nitric oxide causes an extreme drop in blood pressure, resulting in insufficient tissue perfusion and organ failure, syndromes that are associated with many diseases and/or conditions (e.g., septic shock, stroke, over expression of cytokines, allograft rejection, and the like). The overproduction of nitric oxide is triggered by a number of stimuli, such as, the overproduction of inflammatory cytokines (e.g., the overproduction of interleukin-1, interferons, endotoxin, and the like). Additionally, the overproduction of NO has been found to be one of the major side-effects of cytokine therapy (see, for example, Miles et al., in Eur. J. Clin. Invest., 24:287–290 (1994) and Hibbs et al., in J. Clin. Invest., 89:867–877 (1992)). Thus, abnormally elevated nitric oxide levels have been associated with many inflammatory and infectious diseases.

The half-life of NO in vivo is only 3–5 seconds, a short lifetime that makes it very difficult to detect and quantify. Several biophysical techniques have been developed for the measurement of NO levels in aqueous solution. These include chemiluminescence assay (see, for example, Downes et al., Analyst, 101:742–748 (1976)), oxyhemoglobin assay (see, for example, Kelm and Schrader, Cir. Res., 66:1561–1575 (1990)), GC-MS detection (see, for example, Palmer et al., Nature (London), 327:524–526 (1987)), and nitrosyl-hemoglobin formation detected by electron paramagnetic resonance (EPR) spectroscopy at liquid nitrogen temperature (see, for example, Lancaster et al., Proc. Natl. Acad. Sci. USA, 87:1223:1227 (1990)).

Production of NO can also be indirectly detected by measuring its end products, $NO_2^-/NO_3^-$ (see, for example, Palmer et al., supra). None of these techniques in their present forms, however, can be used for in vivo detection of NO production. Recently, an invasive electrochemical microsensor to detect NO levels in blood vessels of healthy human volunteers has been described (see, for example, Vallance et al., Lancet, 346:153–154 (1995)).

Dithiocarbamates are a class of low molecular-weight sulphur-containing compounds that are effective chelators (see, for example, Shinobu et al., Acta Pharmacol et Toxicol., 54:189–194 (1984)). For example, diethyldithiocarbamate (DETC) is used clinically for the treatment of nickel poisoning. Recently, it was found that N-methyl-D-glucamine dithiocarbamate (MGD) chelates with ferrous iron as a two-to-one [$(MGD)_2$-Fe] complex, which in turn interacts strongly with NO, forming a stable and water-soluble complex in aqueous solution, i.e., [$(MGD)_2$-Fe-NO] (see, for example, Lai & Komarov, FEBS Lett., 345:120–124 (1994)). The latter complex gives rise to a sharp three-line spectrum with $g_{iso}=2.04$, characteristic of a nitrosyl-Fe-dithiocarbamate complex which can readily be detected by EPR spectroscopy at ambient temperatures. This method of detecting NO in body fluids in real time has recently been described by Lai in U.S. Pat. No. 5,358,703.

There is, however, still a need in the art for more rapid, preferably non-invasive methods for the detection of nitric oxide in body fluids.

BRIEF DESCRIPTION OF THE INVENTION

In accordance with the present invention, ELISA methods have been developed for the measurement of NO levels in mammalian body fluids utilizing monoclonal antibodies directed against dithiocarbamates and related iron complexes. It has been found that conjugation of dithiocarbamates to a macromolecule, as described herein, produces immunogenic dithiocarbamate-macromolecule derivatives. Such derivatives can be used for the production (e.g., in rodents) of monoclonal antibodies directed against different forms of dithiocarbamates (e.g., free dithiocarbamates, as well as complexes thereof with iron and, optionally, nitric oxide). In contrast, non-derivatized dithiocarbamates alone are not immunogenic.

The simple, easy and non-invasive ELISA methods for measurement of NO levels in body fluids will find a variety of uses, e.g., for diagnosis and monitoring of NO overproduction that has been associated with many inflammatory and infectious diseases.

DETAILED DESCRIPTION OF THE INVENTION

In accordance with the present invention, there are provided methods for rendering low molecular weight dithiocarbamates immunogenic (i.e., methods for preparing immunogenic species from non-immunogenic dithiocarbamates). Invention methods comprise contacting a dithiocarbamate with a macromolecule in the presence of a crosslinking agent under crosslinking conditions.

Any dithiocarbamate can be treated in accordance with the present invention. Presently preferred dithiocarbamates for use herein include compounds having the structure:

$$(R)_2N—C(S)—SH \qquad (I)$$

wherein each R is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or the like, or the two R groups can cooperate to form a 5-, 6- or 7-membered ring including N and the two R groups.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl", refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "heteroaryl" refers to aromatic groups containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "acyl" refers to alkylcarbonyl species.

As employed herein, "halogen" refers to fluoride, chloride, bromide or iodide atoms.

Presently preferred dithiocarbamates contemplated for use in the practice of the present invention are compounds having the structure I, wherein:

one of the R groups is selected from a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl, while the other R group is selected from a $C_1$ up to $C_4$ alkyl or substituted alkyl.

Especially preferred dithiocarbamates contemplated for use in the practice of the present invention are compounds having the structure I, wherein:

one of the R groups is selected from a $C_2$ up to $C_8$ alkyl or substituted alkyl, wherein the substituents are selected from carboxyl, acetyl, pyridinyl, pyrrolidinyl, amino, amido, hydroxy or nitro, while the other R group is selected from methyl, ethyl, propyl or butyl.

The presently most preferred dithiocarbamates contemplated for use in the practice of the present invention are compounds having the structure I, wherein:

one of the R groups is selected from a $C_2$ up to $C_8$ alkyl or substituted alkyl, wherein the substituents are selected from carboxyl, acetyl, amido or hydroxy, while the other R group is selected from methyl, ethyl, propyl or butyl.

A wide variety of macromolecules can be employed in the practice of the present invention, such as, for example polypeptides, polysaccharides, polynucleic acids, and the like. Macromolecules contemplated for use herein can be synthetic, naturally occurring or modified naturally occurring materials.

Polypeptides contemplated for use herein include naturally occurring proteins (such as serum albumin, hemocyanin, ovalbumin, and the like), purified protein derivatives (e.g., a purified protein derivative of tuberculin), recombinant proteins, modified proteins (e.g., cationized BSA), and the like.

Polysaccharides contemplated for use herein include dextran, chitosan, alginates, polymannuronic acid, polymannuronates, hyaluronic acid, chitin, cellulose, starch, glycogen, guar gum, locust bean gum, levan, inulin, cyclodextran, agarose, xanthan gum, carageenan, heparin, pectin, gellan gum, scleroglucan, and the like.

Polynucleic acids contemplated for use herein include naturally occurring double strand DNA, single strand DNA, RNA, synthetic DNA, recombinant DNA, recombinant RNA, and the like.

Crosslinking contemplated by the invention method can be carried out in a variety of ways, i.e., the dithiocarbamate can be crosslinked to a macromolecule by a crosslinking agent via any functionality on the macromolecule. Exemplary functionalities on said macromolecule include amino groups, hydroxy groups, sulfhydryl groups, carboxyl groups, and the like.

Crosslinking agents contemplated for use herein include photoreactive crosslinkers, homobifunctional crosslinkers, heterobifunctional crosslinkers, and the like. Examples of photoreactive crosslinkers are azido compounds, diazo compounds, and the like.

Exemplary azido and diazo compounds include sulfosuccinimidyl (4-azidosalicylamido)hexanoate, azidobenzoyl hydrazide, N-5-azido-2-nitrobenzoyloxysuccinimide, N-4-(p-azido-salicylamido)butyl-3'(2'-pyridyldithio) propionamide, p-azidophenylglyoxal monohydrate, 4-(p-azidosalicylamido) 4-(iodoacetamido)butane, bis[($\beta$-4-azidosalicylamido)ethyl]disufide, N-hydroxysuccinimidyl 4-azidobenzoate, N-hydroxysulfosuccinimidyl 4-azidobenzoate, N-hydroxysuccinimidyl-4-azidosalicylic acid, N-hydroxysulfosuccinimidyl-4-azidosalicylic acid, p-nitrophenyl-2-diazo-3,3,3-trifluoropropionate, 2-diazo-3, 3,3-trifluorpropionyl chloride, N-succinimidyl-(4-azidophenyl)-1,3'-dithiopropionate, sulfosuccinimidyl (4-azidophenyldithio)propionate, sulfosuccinimidyl-2-(7-azido-4-methylcoumarin-3-acetamide) ethyl-1,3'-dithiopropionate, sulfosuccinimidyl-7-azido-4-methylcoumarin-3-acetate, sulfosuccinimidyl-2-(m-azido-o-nitrobenzamido)-ethyl-1,3'-dithiopropionate, and the like.

Bifunctional crosslinkers contemplated for use herein can be further divided into two categories, i.e., homobifunctional crosslinkers and heterobifunctional crosslinkers.

Exemplary homobifunctional crosslinkers include dimethyl adipimidate, dimethyl suberimidate, dimethyl pimilimidate, disuccinimidyl glutarate, disuccinimidyl suberate, bis(sulfosuccinimidyl) suberate, bis(diazobenzidine), ethylene glycobis(succinimidylsuccinate), disuccinimidyl tartrate, disulfosuccinimidyl tartrate, bismaleidohexane, glutaraldehyde, dithiobis(succinimidyl propionate), dithiobis(sulfosuccinimidyl propionate), 1,4-di [3',2'-pyridyldithio(propionamido) butane], N,N'-dicyclohexylcarbodiimide, bis[2-(succinimidyloxycarbonyloxy)ethyl]sulfone, dimethyl 3,3'-dithiobispropionimidate, and the like.

Exemplary heterobifunctional crosslinkers include succinimidyl 4-(N-maleimidomethyl)cyclohexane-1-carboxylate, m-maleimidobenzoyl-N-hydroxysuccinimide ester, succinimidyl-4-(p-maleimidophenyl)butyrate,N-($\gamma$-maleimidobutyryloxy)succinimide ester, N-succinimidyl(4-iodoacetyl) aminobenzoate, 4-succinimidyl oxycarbonyl-$\alpha$-(2-pyridyldithio)toluene, sulfosuccinimidyl-6-[$\alpha$-methyl-$\alpha$-(2-pyridyldithio) toluamido]hexanoate, N-succinimidyl-3-(2-pyridyldithio) propionate, 3-(2-pyridyldithio) propionyl hydrazide, 1-ethyl-3-(3-dimethylaminopropyl) carbodiimide hydrochloride, 3-(p-azidosalicylamido) butylamine, 1,5-difluoro-2,4-dinitrobenzene, N-hydroxysuccinimidyl 2,3-dibromo-propionate, and the like.

When photoreactive crosslinking agents are employed, typical crosslinking conditions comprise exposure to ultraviolet radiation at a temperature in the range of about 4° C. up to about 40° C. for a time in the range of about 0.1 min up to about 10 min.

When bifunctional crosslinking agents are employed, typical crosslinking conditions comprise first contacting the crosslinking agent with either the dithiocarbamate or the macromolecule at a temperature in the range of about 4° C. up to about 40° C. for a time in the range of about 0.1 min up to about 30 min; then subsequently contacting the resulting intermediate with the other of the dithiocarbamate or the macromolecule (whichever was not employed in the initial contacting) at a temperature in the range of about 4° C. up to about 40° C. for a time in the range of about 0.1 min up to about 30 min.

In accordance with another embodiment of the present invention, there are provided immunogenic derivatives of non-immunogenic dithiocarbamates. Such derivatives comprise at least one dithiocarbamate covalently attached to a macromolecule. Such derivatives are capable of forming a complex with iron, which can further complex with nitric oxide. Thus, there are provided immunogenic derivatives of free dithiocarbamate, as well as immunogenic derivatives of the iron-dithiocarbamate complex, [(dithiocarbamate)$_2$Fe], and the nitric oxide-iron-dithiocarbamate complex, [(dithiocarbamate)$_2$Fe—NO].

In accordance with still another embodiment of the present invention, there are provided methods for the production of antibodies against a dithiocarbamate. Invention method comprises immunizing a host animal with a modified dithiocarbamate as described hereinabove. In an alternate aspect, such immunization can be carried out with modified dithiocarbamate which is further complexed with iron. In yet another aspect, such immunization can be carried out with modified dithiocarbamate which is further complexed with iron and nitric oxide.

Preparation of antibodies contemplated herein can readily be accomplished employing standard techniques, as are well known to those of skill in the art, using the invention dithiocarbamate derivatives as antigens for antibody production. For example, polyclonal and monoclonal antibodies can be produced by methods described, for example, in Harlow and Lane, *Antibodies: A Laboratory Manual* (Cold Spring Harbor Laboratory 1988), which is incorporated herein by reference. Altered antibodies such as chimeric, humanized, CDR-grafted or bifunctional antibodies can also be produced by methods well known in the art. Such antibodies can also be produced by hybridoma, chemical synthesis or recombinant methods described, for example, in (Sambrook et al., *Molecular Cloning: A Laboratory Manual* 2d Ed. (Cold Spring Harbor Laboratory, 1989); incorporated herein by reference and Harlow and Lane, supra). Both anti-peptide and anti-fusion protein antibodies can be used. (see, for example, Bahouth et al., *Trends Pharmacol. Sci.* . 12:338 (1991); Ausubel et al., *Current Protocols in Molecular Biology* (John Wiley and Sons, NY 1989) which are incorporated herein by reference).

For example, antibodies raised in rabbits against a dithiocarbamate derivative of the invention recognize the corresponding dithiocarbamate (or iron- or iron-nitric oxide-containing complexes thereof). Antibodies to dithiocarbamates may be obtained, for example, by immunizing three month old male and female white New Zealand rabbits with a suitable derivatized dithiocarbamate. Animals are immunized with the equivalent of 1 mg of the dithiocarbamate antigen according to the procedure of Benoit et al., *Proc. Natl. Acad. Sci. USA*, 79:917–921 (1982). At four week intervals, the animals are boosted by injections of 200 μg of the antigen and bled ten to fourteen days later. After the third boost, antiserum is examined for its capacity to bind radioiodinated antigen prepared by the chloramine-T method and then purified by CMC-ion exchange column chromatography. The antibody molecules are then collected from the mammal and isolated recognized by those of skill in the art, a variety of body fluids can be assayed employing the invention assay.

Exemplary body fluids contemplated for assay include saliva, blood, synovial fluid, urine, tears, and the like.

As used herein, the term "label" refers to single atoms and molecules that are either directly or indirectly involved in the production of a detectable signal. Any label can be linked to or incorporated into an antibody molecule that is part of an antibody or monoclonal antibody composition of the present invention, or used separately.

These atoms or molecules can be used alone or in conjunction with additional reagents. Such labels are themselves well-known in clinical diagnostic chemistry.

Labels contemplated for use herein can be fluorescent labeling agents that chemically bind to antibodies without denaturation to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB-200-SC), and the like. A description of immunofluorescence analytic techniques is found in DeLuca, "Immunofluorescence Analysis", in *Antibody As a Tool*, (Marchalonis et al., eds.), John Wiley & Sons, Ltd., pp. 189–231 (1982), which is incorporated herein by reference.

In a preferred aspect of the invention, the indicating group is an enzyme, such as horseradish peroxidase (HRP), alkaline phosphatase, glucose oxidase, and the like. In such cases where the principal indicating group is an enzyme, additional reagents are required for the production of a visible signal. Such additional reagents for HRP include hydrogen peroxide and an oxidation to the extent desired by well known techniques such as, for example, by using DEAE Sephadex to obtain the IgG fraction.

To enhance the specificity of the antibody, the antibodies may be purified by immunoaffinity chromatography using solid-phase immunizing material. The antibody is contacted with the solid-phase immunizing material for a period of time sufficient for the immunizing material to immunoreact with the antibody molecules to form a solid-phase immunocomplex. The bound antibodies are then separated from the complex by standard techniques.

In accordance with yet another embodiment of the present invention, there are provided antibodies produced as described hereinabove. Such antibodies are capable of specifically binding dithiocarbamate, either as free dithiocarbamate, the iron-dithiocarbamate complex, [(dithiocarbamate)$_2$Fe], and/or the nitric oxide-iron-dithiocarbamate complex, [(dithiocarbamate) $_2$Fe—NO].

In accordance with a still further embodiment of the present invention, there are provided methods for determining NO levels in mammalian body fluids, said method comprising:

contacting an aliquot of body fluid with:
an iron-dithiocarbamate complex,
a dithiocarbamate-selective antibody as described herein, and
a labeled antibody selective for free dithiocarbamate or iron-dithiocarbamate complex, and thereafter
determining the quantity of nitric oxide-containing, iron-containing dithiocarbamate complex, thereby indicating the level of NO in said body fluid.

Contacting contemplated by the above-described method can be carried out in vitro or in vivo. As readily dye precursor such as diaminobenzidine. An additional reagent useful with glucose oxidase is 2,2'-azino-di-(3-ethyl-benzthiazoline-G-sulfonic acid) (ABTS).

In another aspect of the invention, radioactive elements are employed as labeling agents. An exemplary radiolabeling agent is a radioactive element that produces gamma ray emissions. Elements which emit gamma rays, such as $^{124}$I, $^{125}$I, $^{126}$I, $^{131}$I and $^{51}$Cr, represent one class of radioactive element indicating groups. Particularly preferred is $^{125}$I. Another group of useful labeling means are those elements such as $^{11}$C, $^{18}$F, $^{15}$O and $^{13}$N which emit positrons. The positrons so emitted produce gamma rays upon encounters with electrons present in the animal's body. Also useful is a beta emitter, such as $^{32}$P, $^{111}$ indium or $^3$H.

The linking of label to antibodies is well known in the art. For instance, antibody molecules can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, 8(Suppl. 7):7–23 (1978), Rodwell et al., *Biotech.*, 3:889–894 (1984), and U.S. Pat. No. 4,493,795.

Biotin can also be employed as a principal labeling agent. Several molecules of biotin can be chemically linked to one antibody molecule (Gretch et al., *Anal. Biochem.*, 163:270–277 (1987); Warnke et al., *J. Histochem. and Cytochem.*, 28:771–776 (1980); O'Shannessy et al., *Immunol. Lett.*, 8:273–277 (1984)). When biotin is the principal label, additional reagents such as avidin, streptavidin, or modified avidin are required for production of a signal. Avidin and streptavidin each have 4 subunits and each subunit can bind one molecule of biotin. (Biotin binds with high affinity to avidin and related proteins.) The additional reagent is itself covalently linked to another label such as an enzyme of fluorochrome.

The quantity of nitric oxide-containing, iron-containing dithiocarbamate complex formed in the above-described assay can be readily determined employing standard techniques. Those of skill in the art recognize that the method of detection employed will depend on the label employed. Thus, immunofluorescence can be detected, production of an enzymatically catalyzed reaction product can be detected, association of radioactive label with the sample being analyzed can be detected, and the like.

In accordance with a further embodiment of the present invention, there are provided methods to determine the tissue distribution of NO-scavenging dithiocarbamates (and related iron-containing complexes thereof), said method comprising:

contacting a tissue sample or extract therefrom with a dithiocarbamate-selective antibody as described herein, and thereafter
determining which samples form antigen-antibody complex in combination with said antibody.

Formation of antigen-antibody complexes as contemplated by the above-described invention assay can be readily detected in a variety of ways, as can readily be determined by those of skill in the art. For example, association of label (from a labelled antibody) with the sample being tested can be monitored. Alternatively, the formation of a complex having substantially higher molecular weight than the antigen or antibody alone can be monitored.

The invention will now be described in greater detail by reference to the following non-limiting examples.

EXAMPLE 1

Preparation of MGD-BSA Complexes

The crosslinking experiments were performed as follows: One ml of bovine serum albumin (BSA; 0.25 mM in water) was added to a 10-ml beaker containing an aliquot of 100 mM N-hydroxysulfosuccinimidyl-4-azido salicylic acid (Sulfo-NHS-ASA; Pierce Chemical Co) in DMSO. The reaction mixture was incubated at 22° C. for 30 min with slow stirring in the dark. Upon the addition of N-methyl-D-glucamine dithiocarbamate (MGD; 31.1 mg), the solution was irradiated at 365 nm using an UV lamp for 2 min. After irradiation, the solution was applied to a G-25 pre-packed column. The MGD-BSA containing fraction was collected and re-chromatographed once.

EXAMPLE 2

Preparation of [(MGD)$_2$-Fe]-BSA Complexes

The procedures were the same as described above, except that after irradiation, ferrous sulphate (5.56 mg) was added to the purified MGD-BSA complexes prior to column separation. The protein fractions turned dark brown color, indicative of the presence of [(MGD)$_2$-Fe] complexes.

EXAMPLE 3

Preparation of [(MGD)$_2$-Fe—NO]-BSA complexes

The procedures were the same as described above as in the preparation of [(MGD)$_2$-Fe]-BSA complexes, except that an aliquot of NO (2 mM in water) was transferred from a stock solution into the purified [(MGD)$_2$-Fe]-BSA complexes using a gas-tight syringe.

EXAMPLE 4

Preparation of MGD-Hemocycanin, [(MGD)$_2$-Fe]-Hemocyanin and [(MGD)$_2$-Fe—NO]-Hemocyanin Complexes MGD was crosslinked to hemocyanin (Piece Chemical Co.) by following essentially the same procedures as described above for the crosslinking of MGD to BSA. Hemocyanin in lyophilized form (20 mg) was reconstituted into one ml of water prior to adding to MGD solution. The rest of the procedures for the preparations of MGD-hemocyanin, [(MGD)$_2$-Fe]-hemocyanin or [(MGD)$_2$-Fe—NO]-hemocyanin complexes were identical to those for the preparations of MGD-BSA, [(MGD)$_2$-Fe]-BSA, or [(MGD)$_2$-Fe—NO]-BSA complexes.

EXAMPLE 5

Immunization

Female Sprague Dawley rats were immunized both subcutaneously in two different sites and intraperitoneally with a total of 200 μg of [(MGD)$_2$-Fe—NO]-hemocyanin plus 125 μg of R700 adjuvant (RIBI ImmunoChem Research Inc.) which is composed of monophosphoryl Lipid A and synthetic trehalose dicorynomycolate in squalene and Tween-80. Rats were boosted four weeks later (28 days) with the same amount of [(MGD)$_2$-Fe—NO]-hemocyanin plus adjuvant subcutaneously and intraperitoneally. Plasma was collected from the rats six days after boosting and screened by ELISA for reaction with [(MGD)$_2$-Fe—NO]-BSA or BSA alone. The rats which showed the strongest response to [(MGD)$_2$-Fe—NO]-BSA but not BSA were boosted again intravenously and intraperitoneally five weeks after the second immunization (34 days) with 100 μg of [(MGD)$_2$-Fe-NO]-hemocyanin alone.

EXAMPLE 6

Hybridoma Fusion Procedure

Three days after the second boost, the immunized rats were sacrificed and spleen cells fused with the myeloma cells. The fused cells were transferred to 96 well plates and cultured in HAT media. Supernatant from the wells was collected beginning at 10 days after fusion and screened for reaction with the following conjugates by ELISA: MGD-BSA, [(MGD)$_2$-Fe]-BSA, [(MGD)$_2$-Fe-NO]-BSA, and BSA alone respectively. Cells from wells that reacted strongly with a specific conjugate were expanded and aliquots of cells were frozen in liquid nitrogen. The hybridoma cells producing monoclonal antibodies directed against [(MGD)$_2$—Fe—NO], [(MGD)$_2$-Fe] and MGD alone respectively were selected for ELISA assay development.

EXAMPLE 7

Conjugation of Alkaline Phosphatase (AP) to Monoclonal Antibodies

Monoclonal antibodies direct against [(MGD)$_2$—Fe—NO], [(MGD)$_2$-Fe] or MGD alone are conjugated covalently to alkaline phosphatase or horse radish peroxidase with the use of glutaraldehyde (25%) or other crosslinking reagents from Pierce Chemical Company or other companies for conjugation of enzyme to antibody for immunodetection and enzyme immunoassay.

EXAMPLE 8

Reaction of [(MGD)$_2$-Fe] with no in Body Fluids

Small aliquots of fresh body fluids such as blood, saliva or synovial fluid and the like are drawn quickly into syringes pre-loaded with [(MGD)$_2$-Fe] complexes (either in powder form or in liquid). Free NO present in body fluids reacts rapidly with [(MGD)$_2$-Fe] complexes to form [(MGD)$_2$-Fe—NO] complexes, which are stable at ambient temperature.

EXAMPLE 9

ELISA Assay

Aliquots of monoclonal antibodies directed against [(MGD)$_2$-Fe—NO]-hemocyanin in PBS buffer are incubated with polystyrene or polyvinyl chloride ELISA plates. After washing with PBS buffer, the plates are incubated with a bovine serum albumin (BSA) or other coating protein solution in PBS buffer to mask the unreacted surface. Body fluid mixed with the reagent [(MGD)$_2$-Fe] complex in a syringe as described above is introduced onto the coated plates. The reaction between the [(MGD)$_2$-Fe—NO]

complex, if present, in the body fluid and monoclonal antibodies against [(MGD)$_2$-Fe—NO]-hemocyanin coated on the plate would take place to form the antigen-antibody complex. After washings, the second monoclonal antibodies against either the MGD-hemocyanin or [(MGD)$_2$—Fe]-hemocyanin that are cross-linked with alkaline phosphatase enzyme are added to the plates. Upon washings to remove unreacted materials, the substrate is added and the amount of NO present in the form of [(MGD)$_2$-Fe—NO] complex can be measured spectrophotometrically.

While the invention has been described in detail with reference to certain preferred embodiments thereof, it will be understood that modifications and variations are within the spirit and scope of that which is described and claimed.

That which is claimed is:

1. A method for rendering a dithiocarbamate immunogenic, said method comprising contacting said dithiocarbamate with a macromolecule in the presence of a crosslinking agent under crosslinking conditions wherein said dithiocarbamate and said macromolecule are covalently attached via said crosslinking agent, rendering said dithiocarbamate immunogenic.

2. A method according to claim 1 wherein said dithiocarbamate is selected from compounds having the structure:

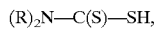
(R)$_2$N—C(S)—SH, wherein each R is independently selected from a C$_1$ to C$_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, or the two R groups can form a 5-, 6- or 7-membered ring including the N and the two R groups.

3. A method according to claim 1 wherein said macromolecule is a polypeptide, a polysaccharide, or a polynucleic acid.

4. A method according to claim 3 wherein said polypeptide is a synthetic, naturally occurring or modified naturally occurring protein.

5. A method according to claim 4 wherein said protein is selected from serum albumin, hemocyanin, ovalbumin or purified protein derivative.

6. A method according to claim 1 wherein said dithiocarbamate is covalently attached to said macromolecule by said crosslinking agent via any functionality on said macromolecule.

7. A method according to claim 6 wherein said functionality on said macromolecule is an amino, hydroxy, sulfhydryl, or carboxyl group.

8. A method according to claim 1 wherein said crosslinking agent is a photoreactive crosslinker or a bifunctional crosslinker.

9. A method according to claim 8 wherein said photoreactive crosslinker is an azido compound or a diazo compound.

10. A method according to claim 9 wherein said photoreactive crosslinker is selected from sulfosuccinimidyl (4-azidosalicylamido)hexanoate, azidobenzoyl hydrazide, N-5-azido-2-nitrobenzoyloxysuccinimide, N-4-(p-azidosalicylamido)butyl-3'(2'-pyridyldithio)propionamide, p-azidophenylglyoxal monohydrate, 4-(p-azidosalicylamido) 4-(iodoacetamido)butane, bis[(β-4-azidosalicylamido)ethyl]disufide, N-hydroxysuccinimidyl 4-azidobenzoate, N-hydroxysulfosuccinimidyl 4-azidobenzoate, N-hydroxysuccinimidyl-4-azidosalicylic acid, N-hydroxysulfosuccinimidyl-4-azidosalicylic acid, p-nitrophenyl-2-diazo-3,3,3-trifluoropropionate, 2-diazo-3,3,3-trifluorpropionyl chloride, N-succinimidyl-(4-azidophenyl)-1,3'-dithiopropionate, sulfosuccinimidyl(4-azidophenyldithio)propionate, sulfosuccinimidyl-2-(7-azido-4-methylcoumarin-3-acetamide)ethyl-1,3'-dithiopropionate, sulfosuccinimidyl-7-azido-4-methylcoumarin-3-acetate, or sulfosuccinimidyl-2-(m-azido-o-nitrobenzamido)-ethyl-1,3'-dithiopropionate.

11. A method according to claim 8 wherein said bifunctional crosslinker is a homobifunctional crosslinker or a heterobifunctional crosslinker.

12. A method according to claim 11 wherein said homobifunctional crosslinker is selected from dimethyl adipimidate, dimethyl suberimidate, dimethyl pimilimidate, disuccinimidyl glutarate, disuccinimidyl suberate, bis (sulfosuccinimidyl) suberate, bis(diazo-benzidine), ethylene glycobis(succinimidylsuccinate), disuccinimidyl tartrate, disulfosuccinimidyl tartrate, bismaleidohexane, glutaraldehyde, dithiobis(succinimidyl propionate), dithiobis(sulfosuccinimidyl propionate), 1,4-di[3',2'-pyridyldithio(propionamido) butane], N,N'-dicyclohexylcarbodiimide, bis[2-(succinimidyloxycarbonyloxy)ethyl]sulfone or dimethyl 3,3'-dithiobispropion-imidate.

13. A method according to claim 11 wherein said heterobifunctional crosslinker is selected from succinimidyl 4-(N-maleimidomethyl)cyclohexane-1-carboxylate, m-maleimidobenzoyl-N-hydroxysuccinimide ester, succinimidyl-4-(p-maleimidophenyl)butyrate,N-(γ-maleimidobutryloxy)succinimide ester, N-succinimidyl(4-iodoacetyl) aminobenzoate, 4-succinimidyl oxycarbonyl-α-(2-pyridyldithio)toluene, sulfosuccinimidyl-6-[α-methyl-α-(2-pyridyldithio) toluamido]hexanoate, N-succinimidyl-3-(2-pyridyldithio) propionate, 3-(2-pyridyldithio) propionyl hydrazide, 1-ethyl-3-(3-dimethylaminopropyl) carbodiimide hydrochloride, 3-(p-azidosalicylamido) butylamine, 1,5-difluoro-2,4-dinitrobenzene or N-hydroxysuccinimidyl 2,3-dibromo-propionate.

14. A method for preparing an immunogenic dithiocarbamate from a non-immunogenic dithiocarbamate, said method comprising contacting said non-immunogenic dithiocarbamate with a macromolecule in the presence of a crosslinking agent under crosslinking conditions wherein said dithiocarbamate and said macromolecule are covalently attached via said crosslinking agent, rendering said dithiocarbamate immunogenic.

15. The product produced by the method of claim 1.

16. An immunogenic dithiocarbamate comprising at least one dithiocarbamate covalently attached via a crosslinking agent to a macromolecule, wherein said dithiocarbamate has the structure

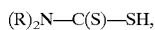
(R)$_2$N—C(S)—SH, wherein each R is independently selected from a C$_1$ to C$_{18}$ alkyl, substituted alkyl, cycloalkyl, substituted cycloalkyl heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, or substituted acyl, or the two R groups can form a 5-, 6- or 7-membered ring including the N and the two R groups, and
wherein said macromolecule is immunogenic when crosslinked with said dithiocarbamate and is not an antibody.

17. An immunogenic dithiocarbamate according to claim 16 wherein said immunogenic dithiocarbamate is further complexed with iron.

18. An immunogenic dithiocarbamate according to claim 17 wherein said immunogenic dithiocarbamate is further complexed with nitric oxide.

* * * * *